(12) United States Patent
Shimoe

(10) Patent No.: US 7,322,968 B2
(45) Date of Patent: Jan. 29, 2008

(54) DISPOSABLE WEARING ARTICLE AND PROCESS FOR MAKING THE SAME

(75) Inventor: Nariaki Shimoe, Kagawa-ken (JP)

(73) Assignee: Uni-Charm Co., Ltd., Shikokuchuo-shi (JP)

( * ) Notice: Subject to any disclaimer, the term of this patent is extended or adjusted under 35 U.S.C. 154(b) by 0 days.

(21) Appl. No.: 10/945,026

(22) Filed: Sep. 21, 2004

(65) Prior Publication Data

US 2005/0038405 A1    Feb. 17, 2005

Related U.S. Application Data

(63) Continuation of application No. PCT/JP03/01803, filed on Feb. 19, 2003.

(30) Foreign Application Priority Data

Mar. 22, 2002   (JP)   ............... 2002-080795

(51) Int. Cl.
    A61F 13/15    (2006.01)
(52) U.S. Cl. ............... 604/390; 604/385.22; 604/386; 604/387; 604/389; 604/391; 604/394; 604/399; 604/385.29; 604/385.3
(58) Field of Classification Search ............... 604/390, 604/385.22, 389, 386, 387, 391, 394, 399, 604/385.29, 385.3
    See application file for complete search history.

(56) References Cited

U.S. PATENT DOCUMENTS

| | | | |
|---|---|---|---|
| 3,874,386 A | 4/1975 | Kozak | |
| 4,177,812 A | 12/1979 | Brown et al. | |
| 4,237,890 A | 12/1980 | Laplanche | |
| 4,317,449 A | 3/1982 | Nowakoski | |
| 4,670,012 A | 6/1987 | Johnson | |
| 5,182,156 A | 1/1993 | Pape et al. | |
| 5,591,521 A * | 1/1997 | Arakawa et al. | 428/352 |
| 6,264,644 B1 | 7/2001 | Igaue et al. | |
| 6,328,725 B2 | 12/2001 | Fernfors | |
| 6,371,949 B1 | 4/2002 | Soga et al. | |
| 6,387,085 B1 * | 5/2002 | Van Gompel et al. | 604/391 |
| 6,475,205 B2 * | 11/2002 | Shimada et al. | 604/385.13 |
| 6,926,704 B2 | 8/2005 | Andersson et al. | |
| 2003/0014030 A1 | 1/2003 | Andersson et al. | |
| 2004/0194879 A1 | 10/2004 | Ohiro et al. | |
| 2005/0070868 A1 * | 3/2005 | Ito et al. | 604/385.01 |
| 2006/0206092 A1 * | 9/2006 | Shimoe | 604/390 |

FOREIGN PATENT DOCUMENTS

| | | |
|---|---|---|
| EP | 0623330 | 11/1994 |
| GB | 1 441 567 | * 7/1976 |
| JP | 50-109041 A | 8/1975 |

(Continued)

Primary Examiner—Tatyana Zalukaeva
Assistant Examiner—Ginger Chapman
(74) Attorney, Agent, or Firm—Lowe Hauptman Ham & Berner LLP

(57) ABSTRACT

A disposable wearing article is provided on its garment facing surface with tape fasteners. The tape member forming each of the tape fastener has a fixed end portion and a free end portion adapted to be taken between the fingers longitudinally opposed to each other. The free end portion at least partially extend beyond the lateral edge of the wearing article.

8 Claims, 13 Drawing Sheets

| FOREIGN PATENT DOCUMENTS | | | | |
|---|---|---|---|---|
| JP | 5-39531 | 5/1993 | | |
| JP | 05-039531 U | 5/1993 | | |
| JP | 06-077719 U | 11/1994 | | |
| JP | 8-507699 | 8/1996 | | |
| JP | 9-253125 | 9/1997 | | |
| JP | 10/085254 | 4/1998 | | |
| JP | 10085254 | * | 7/1998 | |
| JP | 10-211231 A | 8/1998 | | |
| JP | 2000-502573 | 3/2000 | | |
| JP | 2001-46436 A | 2/2001 | | |
| JP | 2001-178777 A | 7/2001 | | |
| WO | 94/09736 | 5/1994 | | |
| WO | 0113842 | 3/2001 | | |
| WO | 03/022195 | 3/2003 | | |

\* cited by examiner

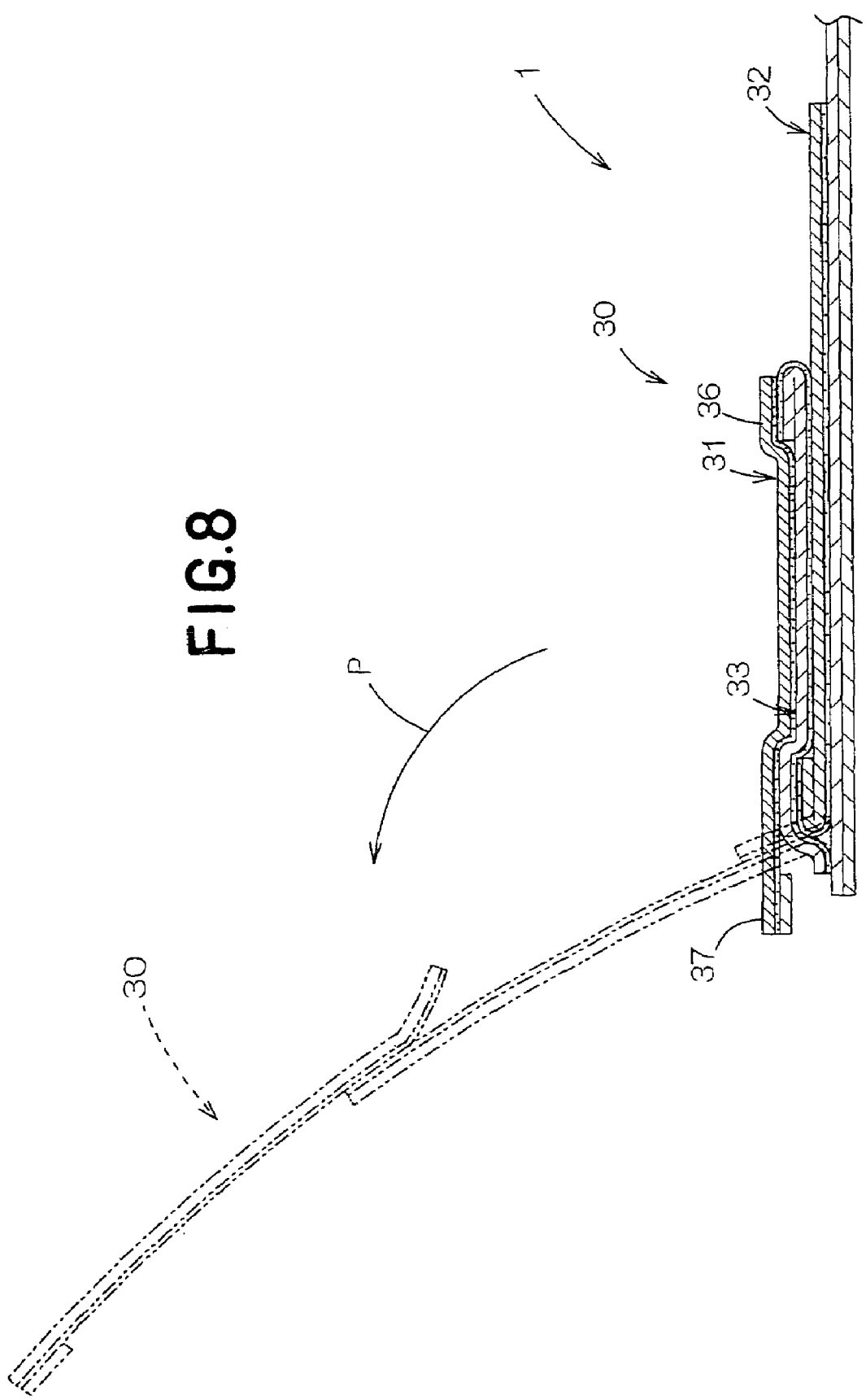

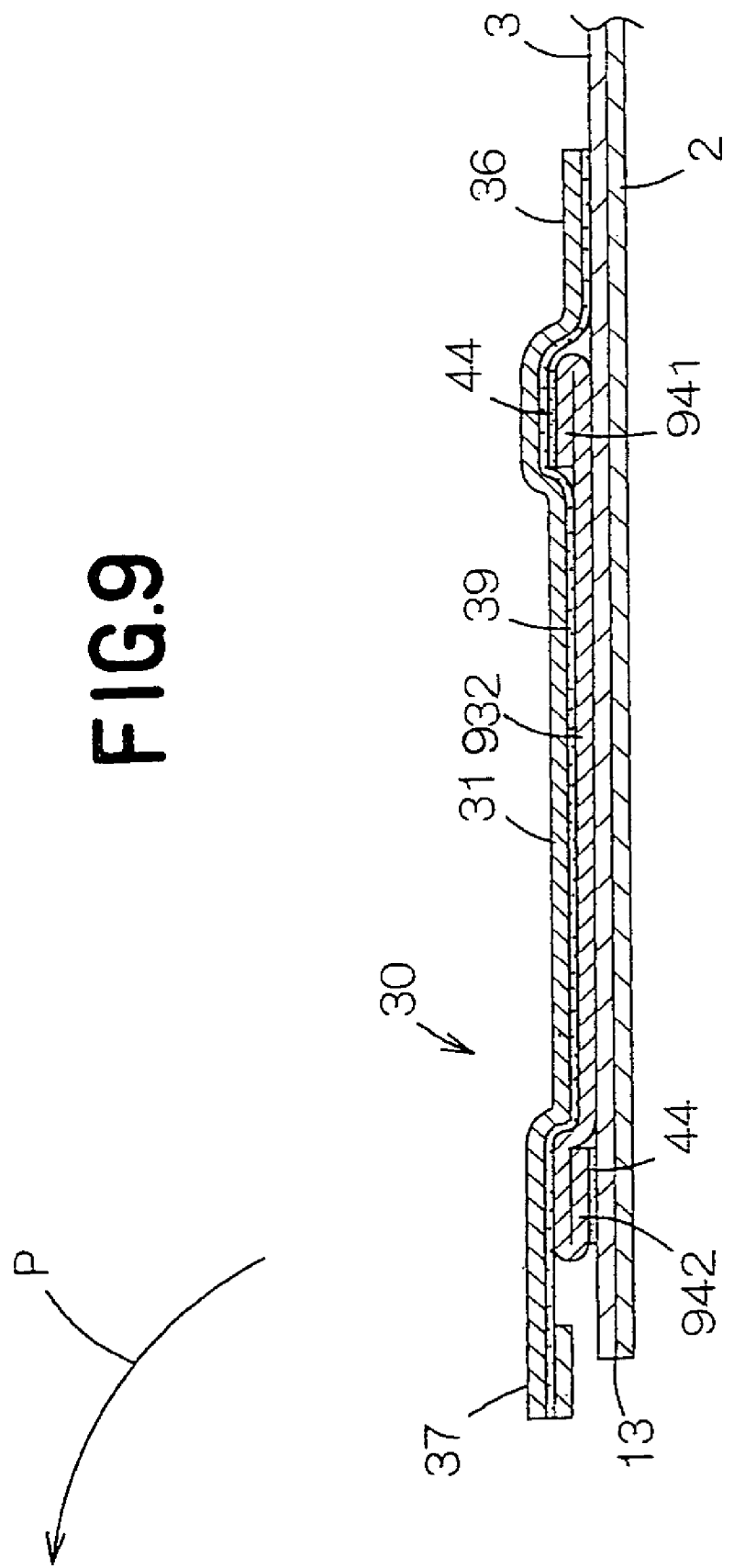

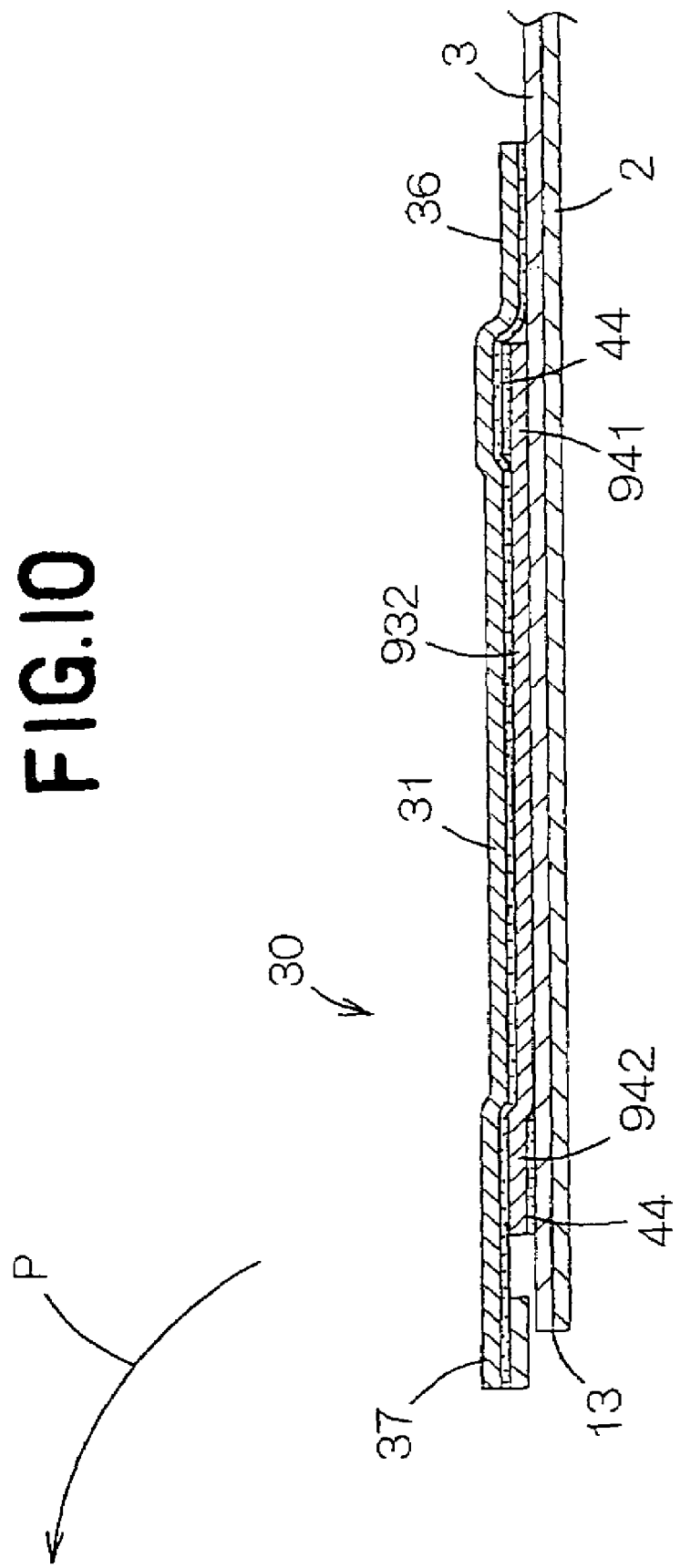

DISPOSABLE WEARING ARTICLE AND PROCESS FOR MAKING THE SAME

TECHNICAL FIELD OF THE INVENTION

This invention relates to a disposable wearing article having tape fasteners and a process for making the same.

BACKGROUND ART OF THE INVENTION

The pants-type disposable diaper disclosed in Japanese Utility Model Application No. 1994-77719A comprising a liquid-pervious topsheet, a liquid-impervious backsheet and a liquid-absorbent member interposed between these two sheets wherein the front and rear waist regions of this diaper are joined together to form a waist-hole and leg-holes. This known pants-type diaper is provided in an intermediate region defined between the waist-hole and the leg-holes with elastic members adapted to contract in a waist-surrounding direction and thereby form gathers in the waist-surrounding direction. Tape fasteners respectively having distal ends are attached to the outer surface of the backsheet so that the distal ends are oriented in the waist-surrounding direction.

In the pants-type diaper disclosed in the above-cited Application, the tape fasteners are attached to side flaps in which the absorbent member is not present. The tape fasteners are usually made of low stiffness tape material and, if a contractile force of the waist-surrounding elastic members is relatively high, these tape fasteners are apt to be deformed and thereby to make it difficult to take the distal ends between fingers at once. In addition, the tape fasteners lie inside transversely opposite lateral edges of the diaper and therefore it is difficult to find the distal ends on the side flaps and to take these distal ends between fingers at a glance.

DISCLOSURE OF THE INVENTION

It is an object of this invention to improve such a wearing article so that distal ends of the respective tape fasteners attached to the wearing article may be easily and quickly taken between fingers.

In accordance with this invention, there is provided a disposable wearing article having a wearer's body facing surface and a garment facing surface, front and rear ends extending in a transverse direction and a pair of lateral edges extending in a longitudinal direction orthogonal, and a crotch region, a front waist region and a rear waist region. The article comprises tape fasteners provided on the garment facing surface in vicinities of the lateral edges in one of the front and rear waist regions. Each of the tape fasteners comprises having a fixed end portion permanently joined to the garment facing surface and a free end portion longitudinally opposed to the fixed end portion and adapted to be taken between fingers so that the tape member is unfolded from the fixed end portion toward the free end portion as the free end portion is taken between fingers and pulled, and a lower surface of the tape member destined to face the garment facing surface is at least partially coated with an adhesive agent, at least a part of the free end portion extending outwardly beyond the lateral edge and upper and lower surfaces of the part being of non-adhesive nature.

This invention includes the following embodiments.

The tape member is in a folded state so that the tape member is unfolded from the fixed end portion toward the free end portion when the article is actually used, and comprises, in such a folded state, a first tape section defining a top layer of the folded tape member and having the free end portion and a first end portion longitudinally opposed to the free end portion and a second tape section underlying the first tape section so as to face the garment facing surface and having the fixed end portion and a second end portion longitudinally opposed to this fixed end portion and connected to the first end portion of the first tape section.

The first end portion of the first tape section extending from the free end portion to the first end portion includes a prolongation extending inwardly with respect to the article beyond the second end portion of the second tape section and the prolongation is releasably joined to the garment facing surface.

A third tape section is interposed between the first tape section and the second tape section to connect these first and second tape sections to each other, the third tape section having one end portion connected to the first end portion of the first tape section, the other end portion opposed to the one end portion and connected to the second end portion of the second tape section, and an intermediate portion defined between the one end portion and the other end portion and releasably joined to at least one of the first tape section and the second tape section so that these first-third tape sections has a Z- or inverted Z-shape as the tape member is folded.

The first end portion of the first tape section extends beyond the one end portion of the third tape section in the transverse direction and is releasably joined to the fixed end portion of the second tape section extending beyond the one end portion of the third tape section in the transverse direction.

The disposable wearing article is a pants-type disposable diaper composed of a front waist region, a rear waist region and a crotch region extending between these two waist regions, the front and rear waist regions being connected to each other in vicinities of lateral edges thereof so as to define a waist-hole and a pair of leg-holes, the tape fasteners being attached to the vicinities surface of the front or rear waist region in vicinities of the respective lateral edges so that the longitudinal direction of the tape fasteners coincide with a waist-surrounding direction of the diaper and the free end portions of the respective tape fasteners may at least partially extend outwardly in the waist-surrounding direction beyond the lateral edges of the front or rear waist region.

The disposable wearing article further includes, in the front and rear waist regions and the crotch region, a liquid-absorbent core having a wearer's body facing surface and flaps formed from sheet members extending outwardly from a peripheral edge of the core wherein the tape fasteners are attached to the garment facing surface in the flaps.

Elastic members are attached in a stretched state to one of the front and rear waist regions provided with the tape fasteners so as to extend in the transverse direction between the lateral edges of the waist region and the tape fasteners are attached to the garment facing surface in the front or rear waist region so as to cover the elastic members from outside.

The garment facing surface to which the tape fasteners are attached is made of a sheet being elastically stretchable in the transverse direction.

The free end portions at least partially extend outwardly beyond the lateral edges by 0.7 mm or more.

In accordance with this invention, there is also provided a process for making a disposable wearing article having a wearer's body facing surface and a garment facing surface; front and rear ends extending in a transverse direction and a pair of lateral edges extending in a longitudinal direction orthogonal to the transverse direction; a crotch region, a front waist region and a rear waist region; one of the front and rear waist regions being provided on the garment facing surface in vicinities of the lateral edges with tape fasteners adapted to be unfolded outwardly from one of the front and rear waist regions in the transverse direction beyond the lateral edges.

The process further comprises the steps of feeding a sheet forming the garment facing surface to which the tape fasteners are attached, including zones destined to define the lateral edges of the wearing article so that a plurality of the sheets are connected one to another along the zones destined to define the lateral edges and thereby to form a continuum of the sheets which is elastically stretchable in the transverse direction in the vicinity of the zones destined to define the lateral edges in the transverse direction, applying a first adhesive agent to a single tape member having upper and lower surfaces on the lower surface at longitudinally opposite end portions except for a longitudinally middle portion to permanently join the end portions to the garment facing surface, applying a second adhesive agent to zones defined between the middle portion and respective the end portions to releasably join the zones to the garment facing surface so as to form an adhesive tape unit, feeding the tape unit onto one side of the continuum of the sheet so that a longitudinal direction of the tape unit coincides with the transverse direction and the middle portion extends across the zone destined to define the lateral edge; joining the tape unit to the one side by means of the first adhesive agent, then cutting the continuum of the sheet together with the tape unit along the zone destined to define the lateral edge to obtain individual sheets each forming the garment facing surface which has contracted in the transverse direction more remarkably than the tape unit in vicinities of the lateral edges and joining the tape fasteners to the sheet in vicinities of the lateral edges to obtain the tape fasteners at least partially extending outwardly beyond the lateral edges.

This invention of the process includes the following embodiments.

The sheet is elastically stretchable in the transverse direction and fed in the transverse direction in an elastically stretched state.

The sheet comprises a non-stretchable sheet and thread-like elastic members bonded to the sheet while these thread-like elastic members are being stretched in the transverse direction.

The tape fasteners at least partially extend outwardly beyond the lateral edges by 0.7 mm or more.

BRIEF DESCRIPTION OF THE DRAWINGS

FIG. 8 is a view similar to FIG. 2 but showing one preferred embodiment of this invention;

FIG. 9 is a view similar to FIG. 2 but showing another preferred embodiment of this invention;

FIG. 10 is a view similar to FIG. 2 but showing still another preferred embodiment of this invention;

DESCRIPTION OF THE BEST MODE FOR WORKING OF THE INVENTION

Details of the disposable wearing article and a process for making the same according to this invention will be more fully understood from the description given hereunder in reference to the accompanying drawings.

Figure 1:
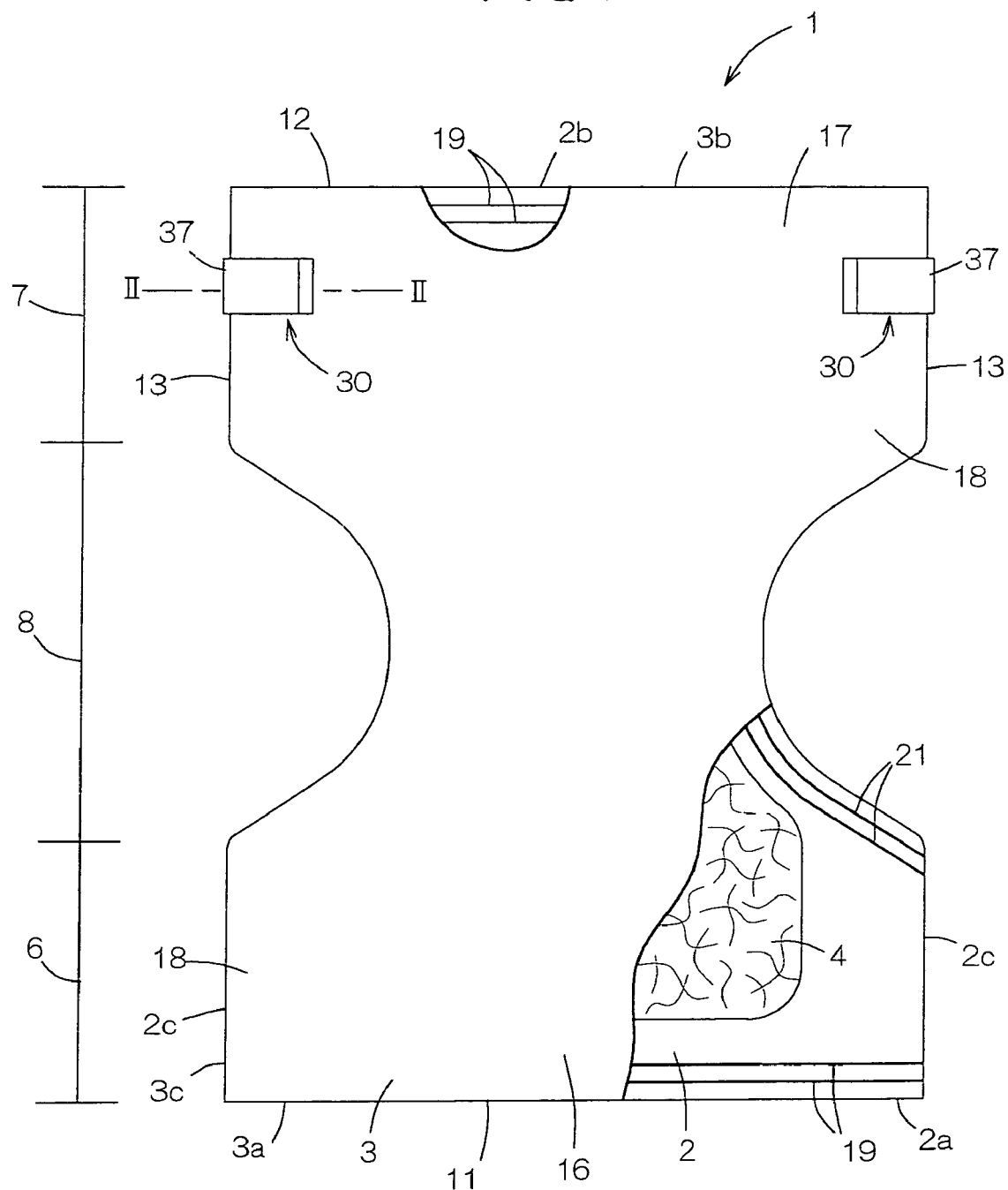
FIG. 1 is a partially cut away plan view showing a disposable diaper as a typical embodiment of this invention.
Figure 2:
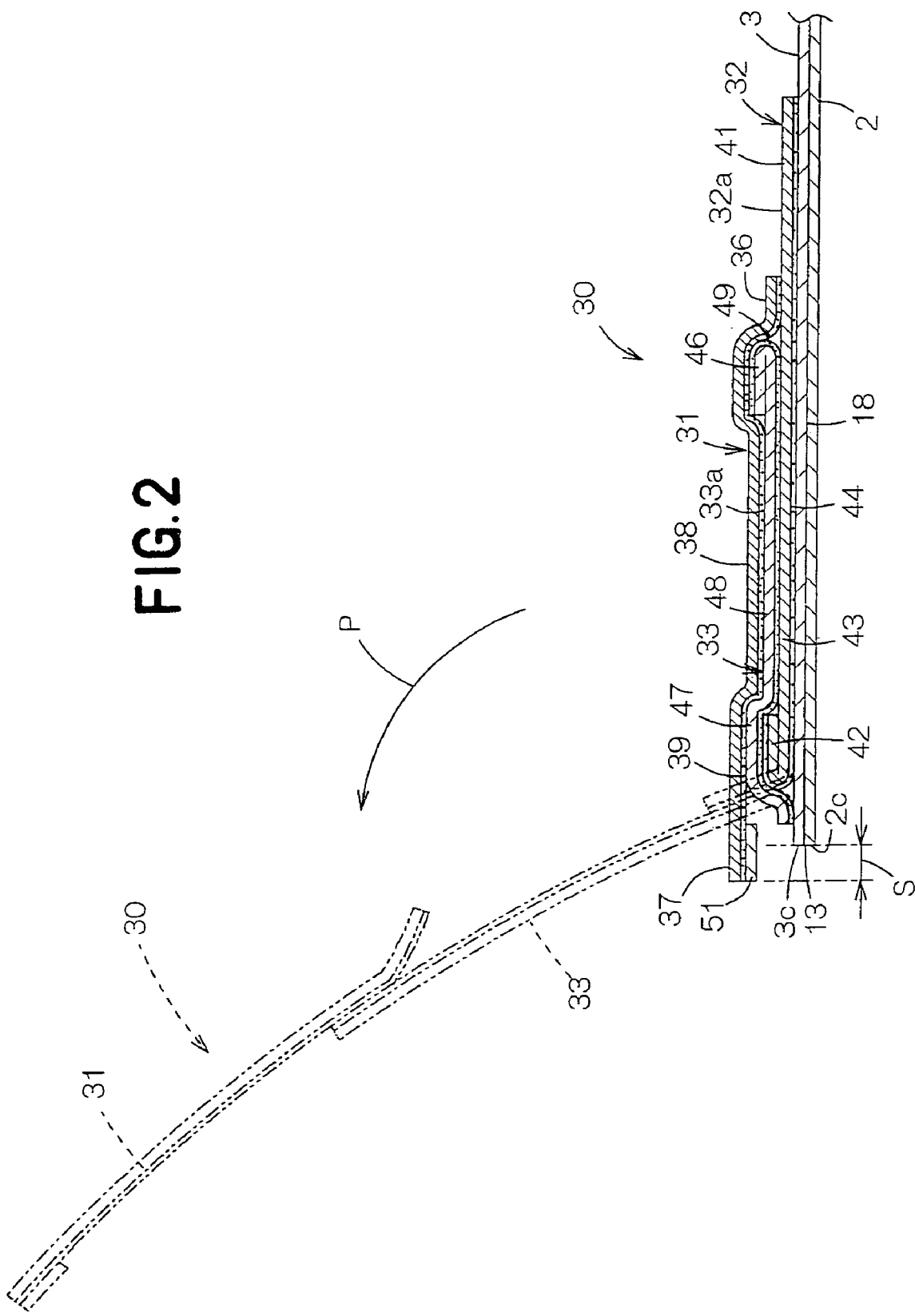
FIG. 2 is a sectional view taken along a line II-II in FIG. 1.

FIG. 1 is a partially cut away plan view showing an open-type disposable diaper 1 and FIG. 2 is a sectional view taken along a line II-II in FIG. 1. The diaper 1 comprises a liquid-pervious topsheet 2 facing the wearer's body, a liquid-impervious backsheet 3 facing the wearer's clothes and a liquid-absorbent core 4 interposed between these two sheets 2, 3. FIG. 1 shows this diaper 1 with the backsheet 3 lying on the upper side and the topsheet 2 lying on the lower side. The diaper 1 is contoured by front and rear ends 11, 12 extending in parallel to each other in a transverse direction (in a horizontal direction as viewed in FIG. 1) and a pair of lateral edges 13 extending in parallel to each other in a longitudinal direction which is orthogonal to the transverse direction. The diaper 1 is composed of, in the longitudinal direction, a crotch region 8, a front waist region 6 extending from the crotch region 8 to the front end 11 and a rear waist region 7 extending from the crotch region 8 to the rear end 12. In the crotch region 8, the lateral edges 13 curve inwardly in the transverse direction of the diaper 1. Portions of the top- and backsheets 2, 3 extending outwardly beyond a peripheral edge of the core 4 are overlaid and joined together by means of hot melt adhesive agents (not shown) to form a front end flap 16, a rear end flap 17 and side flaps 18. In the front and rear end flaps 16, 17, waist-surrounding elastic members 19 are bonded in a stretched state to the inner surface of at least one of the top- and backsheets 2, 3. In the side flaps 18, leg-surrounding elastic members 21 are stretched along the curving sections of the respective lateral edges 13 and bonded in such a stretched state to the inner surface of at least one of the top- and backsheets 2, 3. Tape fasteners 30 are attached to the backsheet 3 of the side flaps 18 in the rear waist region 7 in the vicinity of the respective lateral edges 13. The tape fasteners 30 are folded so that these fasteners 30 maybe unfolded so as to extend outwardly beyond the respective lateral edges 13. The top- and backsheets 2, 3 respective have front and rear ends 2a, 2b, 3a, 3b and lateral edges 2c, 3c defining the front and rear ends 11, 12 and the lateral edges 13 of the diaper 1.

As will be apparent from FIG. 2, each of the tape fasteners 30 comprises an upper tape section 31, a lower tape section 32 and an intermediate tape section 33 lying between these two tape sections 31, 32 and connecting to them to each other. The upper tape section 31 has an inner end portion 36 lying inside the diaper 1, an outer end portion 37 at least partially extending outwardly beyond the lateral edge 13, and an intermediate potion 38 lying inside the lateral edge 13. These portions 36-38 are coated on the lower surfaces thereof with a second self-adhesive agent 39. In FIG. 2, a dimension by which the outer end 37 extends outwardly beyond the lateral edge 13 is indicated by S and this dimension S in the diaper 1 is preferably 0.7 mm or longer. The lower tape section 32 lies inside the lateral edge 13 and is opposed to the surface of the diaper 1 facing the wearer's clothes. The lower tape section 32 also has an inner end portion 41, an outer end portion 42 and an intermediate portion 43. In the case of the lower tape 32 of the tape fastener 30 comprising three tape sections 31, 32, 33 as illustrated, at least the inner end portion 41 functions as a fixed end portion of the tape fastener 30 and is firmly fixed to the backsheet 3 by means of first adhesive agent 44. In the preferable embodiment of the lower tape section 32 as shown, the inner end portion 41, the intermediate portion 43 and the outer end portion 42 except for its zone in which the outer end portion 42 is connected to the intermediate tape section 33 are fixed to the backsheet 3 by means of the first adhesive agent 44 with which these portions are coated. The lower tape section 32 has its outer end portion 42 partially connected to the intermediate tape section 33 by means of the first adhesive agent 44. The intermediate tape section 33 also lies inside the lateral edge 13 and has an inner end portion 46, an outer end portion 47 and an intermediate portion 48. These portions are coated on the lower surfaces thereof with a third self-adhesive agent 49.

Of the upper tape section 31, a zone of its inner end portion 36 extending inwardly beyond the inner end portion 46 of the intermediate tape section 33 is temporarily bonded to the surface of the diaper facing the wearer's clothes, in the case of the illustrated embodiment, to the upper surface 32a of the lower tape section 32 and firmly bonded to the upwardly folded inner end portion 46 of the intermediate tape section 33. The second self-adhesive agent with which the upper tape section 31 is coated is covered with a film strip 51 on an appropriate area of the outer end portion 37 at least including the area extending outwardly beyond the lateral edge 13 by a dimension S in the longitudinal direction of the upper tape section 31. In this way, the outer end 37 becomes substantially non-adhesive on its both surfaces and thereby forms a free end portion of the tape fastener 30 destined to be taken between fingers. The intermediate portion 38 of the upper tape section 31 is temporarily bonded to upper surface 33a of the intermediate tape section 33 underlying the intermediate portion 38 of the upper tape 31. The intermediate tape section 33 except the inner end portion 46 bonded to the upper tape section 31 and the outer end portion 47 bonded to the outer end portion 42 of the lower tape section 32, i.e., the intermediate portion 48 thereof is temporarily bonded to upper surface 32a of the lower tape section 32 by means of the third self-adhesive agent 49. It should be noted here that the intermediate tape section 33 may be temporarily bonded to any one of the upper tape section 31 and the lower tape section 32 without departing from the scope of this invention.

The upper tape section 31, the intermediate tape section 33 and the lower tape section 32 are thus assembled as a continuous member in a Z-shape folded state prior to use of the article. The outer end portion 37 of the upper tape section 31 may be taken between fingers together with the film strip 51 and pulled outwardly of the diaper 1 as indicated by an arrow P to separate the temporarily bonded portions one from another and thereby to unfold the tape fastener 30 so that the upper tape section 31 and the intermediate tape section 33 may extend as indicated by imaginary lines. To facilitate the second self-adhesive agent 39 to be peeled off from the lower tape section 32 and the intermediate tape section 33 and to facilitate the third self-adhesive agent 49 to be peeled off from the lower tape section 32, adhesive force of the second adhesive agent 39 and third self-adhesive agent 49 may be adjusted to be lower than that of the first adhesive agent 44 and/or these tape sections 32, 33 may be previously coated with silicone oil or the like. In such tape fastener 30, the outer end portion 37 of the upper tape section 31 extends outwardly beyond the lateral edge 13 of the diaper 1 and therefore the outer end portion 37 of the fastener 30 can be quickly taken between fingers even when a plurality of gathers are formed around the waist of the diaper 1 as the elastic members 19 contract and consequently it becomes difficult to find the tape fastener 30 from these gathers. To ensure such effect, it is sufficient that merely a part of the outer end portion, for example, outer end corners of the upper tape section 31 extend outwardly from the lateral edge 13 by 0.7 mm or more. The inner end portion 36 of the upper tape section 31 and the intermediate tape section 33 are detachably attached to the lower tape section 32 but not directly to the backsheet 3, so there is no anxiety that the backsheet 3 might be damaged even if such detachable attachment is repeated.

Figure 3:
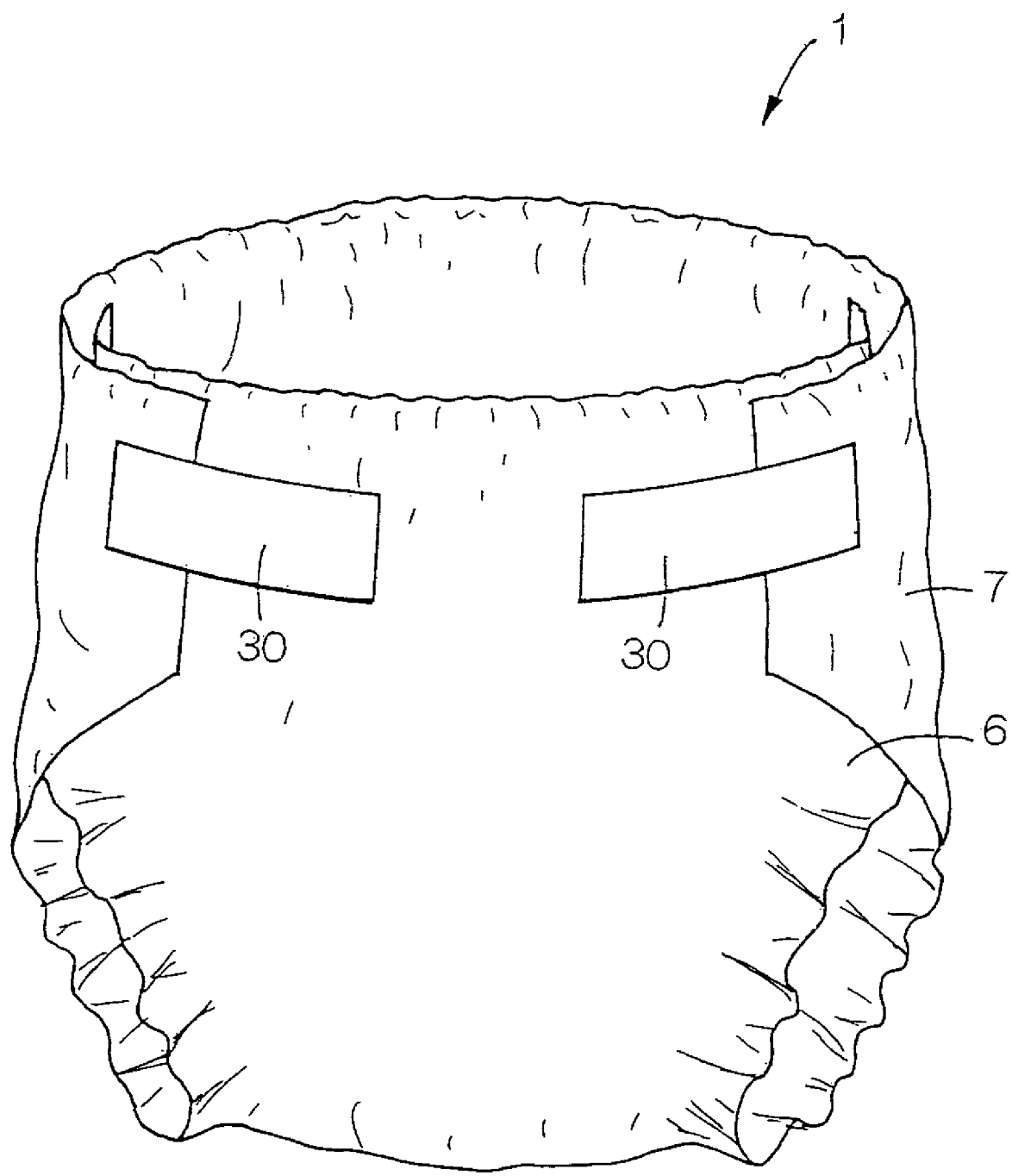
FIG. 3 is a diagram illustrating a manner in which the tape fasteners are used.
Figure 4:
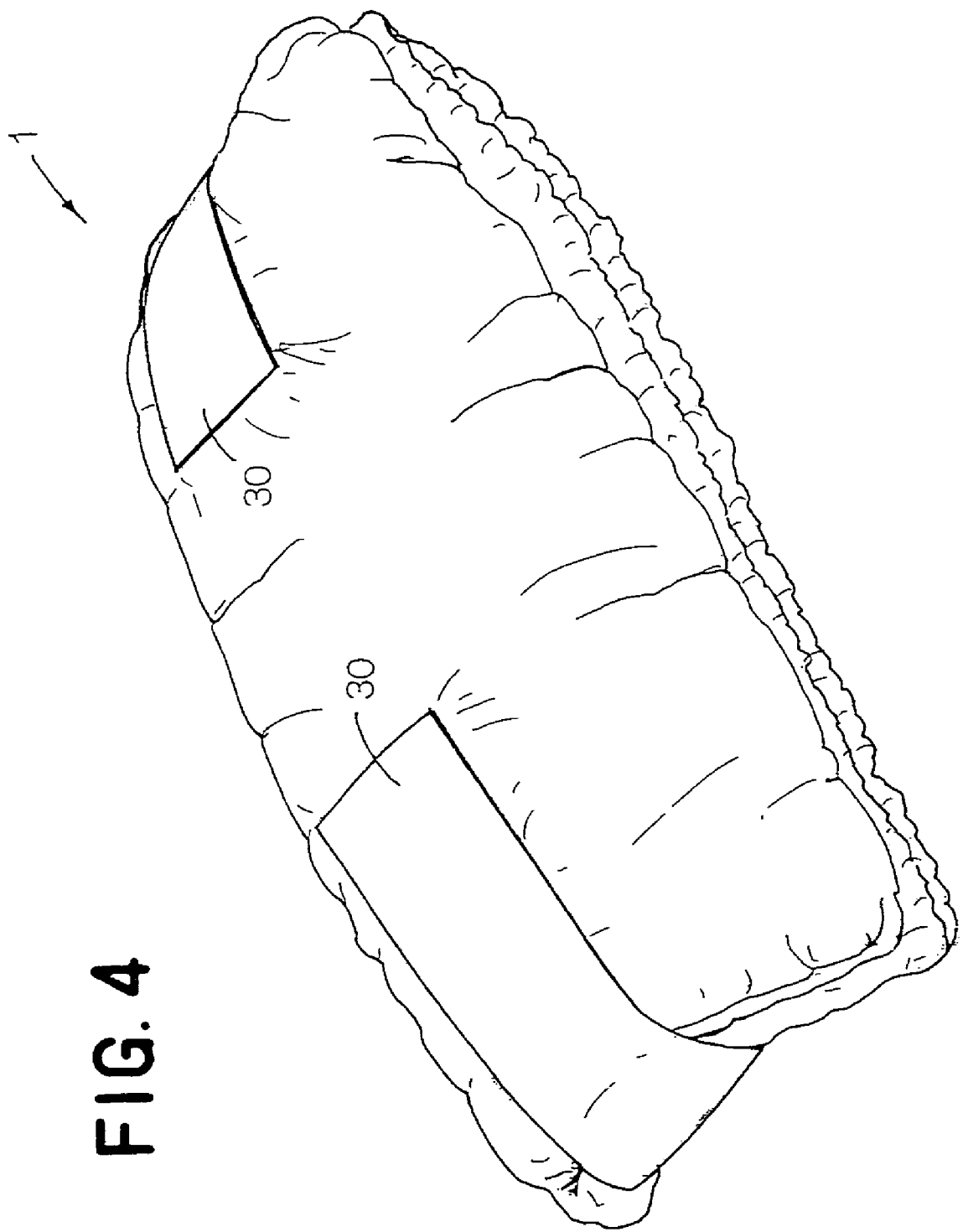
FIG. 4 is a diagram illustrating another manner in which the tape fasteners are used.

FIGS. 3 and 4 are diagrams illustrating manners in which the tape fasteners 30 are used. FIG. 3 shows the diaper 1 put on the wearer's body with the tape fasteners 30 unfolded outwardly from the rear waist region 7 and temporarily bonded to the surface of the front waist region 6 facing the wearer's clothes by means of the second self-adhesive agent 39. FIG. 4 shows the used diaper 1 rolled up and retained by the tape fasteners 30 in such a rolled up state. In this manner, the tape fasteners 30 are useful not only for putting the diaper 1 on the wearer's body but also for rolling up and disposal of the used diaper 1.

Figure 5:
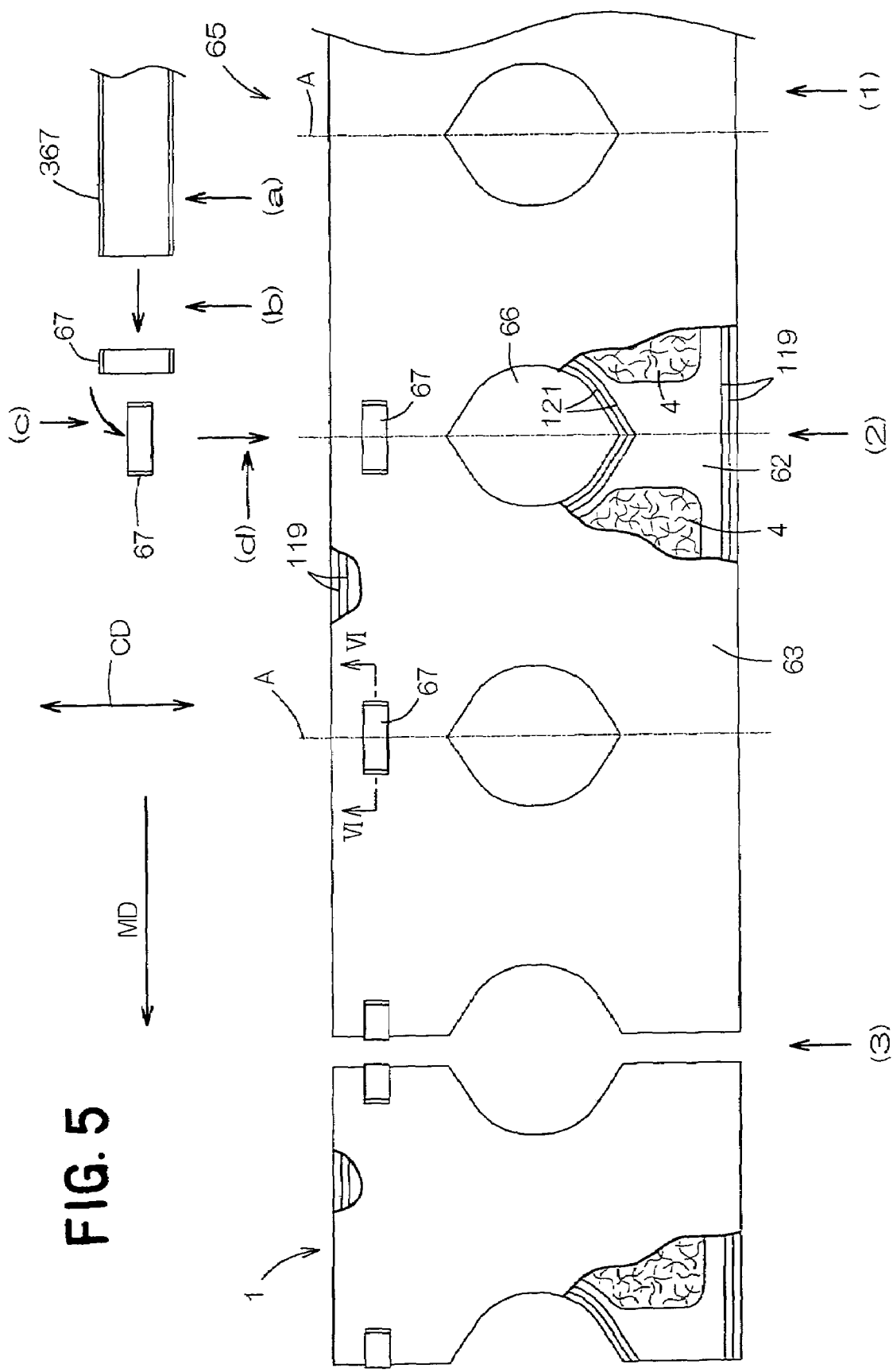
FIG. 5 is a diagram illustrating a part of the process for making the disposable diaper.

FIG. 5 is a diagram illustrating a part of the process for continuously making the diaper 1 of FIG. 1. In a series of steps (1)-(3) indicated in a lower part of FIG. 5, a leftward direction is designates as a machine direction MD. In the step (1), continuum of diapers comprising continuous liquid-pervious web 62, continuous liquid-impervious web 63 and cores 4 interposed between the web 62 and the web 63 so as to be arranged intermittently at desired intervals in the machine direction MD is fed in the direction MD. The web 62 comprises a plurality of the topsheets 2 successively connected one to another along transversely opposite lateral edges 2c of the respective topsheets 2 and defines a lower layer as viewed in FIG. 5. Similarly, the web 63 comprises a plurality of the backsheets 3 successively connected one to another along transversely opposite lateral edges 3c of the respective backsheets 3 and defines an upper layer as viewed in FIG. 5. Around the respective cores 4, these two webs 62, 63 are overlaid and joined together by means of hot melt adhesive agents (not shown). Between these two webs 62, 63, in addition to the cores 4, thread-like waist-surrounding elastic members 119 and leg-surrounding elastic members 121 are interposed and bonded to these webs in a stretched state. The web 63 is elastically stretchable in the machine direction MD and bonded to the web 62 as the web 63 is being stretched at a desired percentage in the machine direction MD. The continuum of diapers 65 has a dimension in a cross direction CD orthogonal to the machine direction MD corresponds to a longitudinal dimension of the diaper 1 and imaginary lines A in FIG. 5 correspond to the lateral edges 13 of the individual diapers 1. The core 4 lies in a middle zone between each pair of the adjacent imaginary lines A, A and circular portions are cut out from the webs 62, 63 overlaid each other in substantially middle zones on the respective imaginary lines A to form openings 66. Even after these openings 66 have been formed, conveyor means (not shown) for the continuum 65 provides a vacuum suction effect under which the web 63 remains stretched in the machine direction MD.

In sub-steps (a)-(d) of the step (2) as indicated on upper part of FIG. 5, tape fastener units 67 are successively fed and attached to the continuum 65 running in the machine direction MD so that the units 67 may straddle the imaginary lines A, respectively.

In the step (3), the continuum 65 of diapers is cut together with the units 67 along the imaginary lines A to obtain the individual diapers 1 each shown in FIG. 1. In the diaper 1 obtained in this manner, the web 63 which has been in a stretched state in the continuum 65 elastically contracts in the transverse direction to form the backsheet 3. Contraction of the web 63 causes the web 62 bonded to the web 63 to contract with formation of gathers. Thereupon, a peripheral edge of the opening 66 is bisected to form the circular arc-shaped lateral edges 13 of the diaper 1 in its crotch region 8. In the diaper 1 in FIG. 5, the waist-surrounding elastic members 119 as well as the leg-surrounding elastic members 121 are in a stretched state.

In a series of sub-steps (a)-(d) indicated on the upper part of FIG. 5, the individual units 67 are formed. The units 67 are non-stretchable in the longitudinal direction thereof. In the sub-step (a), continuum of the units 367 destined to be cut into the individual units 67 is fed from the right to the left in FIG. 5. In the sub-step (b), the continuum 367 is transversely cut into the individual units 67. In the sub-step (c), the unit 67 obtained in the sub-step (b) is rotated by 90° so that the longer sides of the respective unit 67 may extend in the machine direction MD. In the sub-step (d), the unit 67 having been rotated in this manner is fed to the continuum of diapers 65. It is possible to feed the continuum of units 367 in the cross direction CD instead of feeding it in the machine direction MD as in the illustrated embodiment. In this case, the individual units 67 obtained by cutting the continuum 367 may be fed to the continuum of diapers 65 in the cross direction CD.

Figure 6:
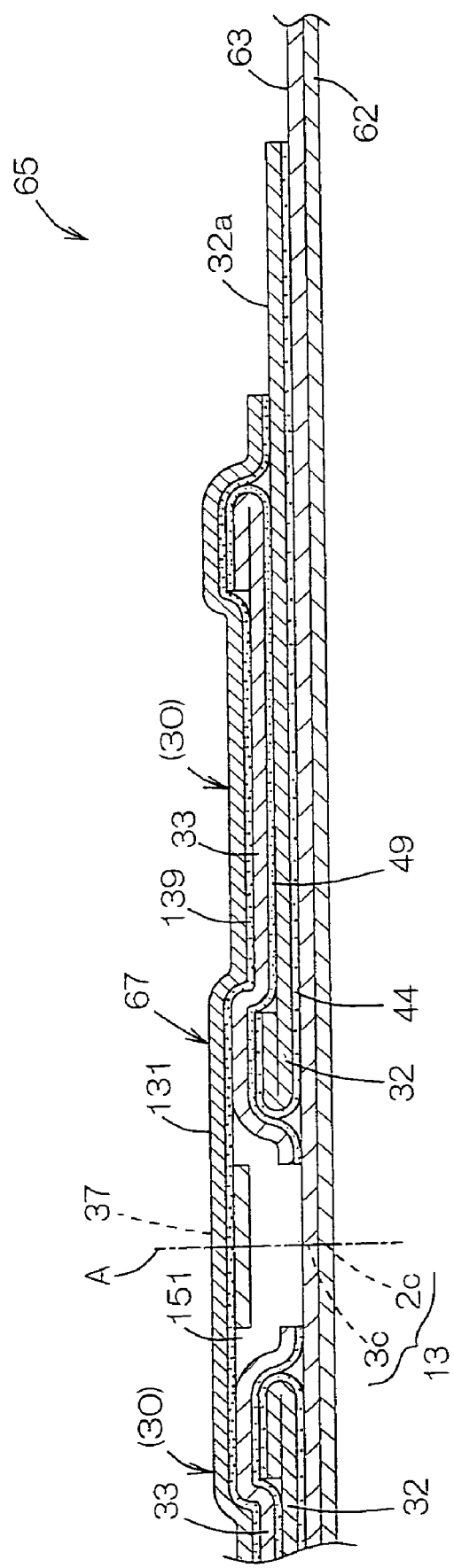
FIG. 6 is a sectional view taken along a line VI-VI in FIG. 5.

FIG. 6 is a sectional view of continuous diapers 65 to which the units 67 shown in FIG. 5 have been attached, as taken along a line VI-VI. The unit 67 is symmetric about an imaginary line A and its substantially left half is not illustrated. This unit 67 comprises the first tape section 131 extending in the machine direction MD across the imaginary line A, the lower tape section 32 bonded to the liquid-impervious web 63 by means of the first adhesive agent 44 on both sides of the imaginary line A and the intermediate tape section 33 temporarily bonded to the upper surface 32a of the lower tape section 32 by means of the third adhesive agent 49 on both sides of the imaginary line A. The first tape section 131 is temporarily bonded to the upper surface of the intermediate tape section 33 by means of the self-adhesive agent 139 which is, in turn, covered with the plastic film strip 151 in the vicinity of the imaginary line A corresponding to the longitudinally middle zone of the unit 67. The continuum of diapers 65 is cut together with the unit 67 along the imaginary line A. After having been cut, the web 63, the web 62 bonded to the web 63 and the waist-surrounding elastic members 119 contract together in the horizontal direction as viewed in FIG. 6, i.e., in the transverse direction of the diaper 1 but the unit 67 does not contract. Consequently, the individual diaper 1 and the tape fasteners 30 attached thereto as shown in FIG. 1 is obtained. In the individual diaper 1 obtained in this manner, the liquid-pervious web 62 and the liquid-impervious web 63 define the topsheet 2 and the backsheet 3, respectively, and the lateral edges 2c, 3c of the top- and backsheets 3 as well as the lateral edges 13 of the diaper 1 are formed along each pair of the adjacent imaginary lines A. The first tape section 131, the self-adhesive agent 139 and the plastic film strip 151 are bisected along the imaginary line A to form the upper tape section 31, the second self-adhesive agent 39 and the film strip 51 of the tape fastener 30 in FIG. 2. The lower tape section 32 and the first adhesive agent 44 respectively correspond to the lower tape section 32 and the first adhesive agent 44 in FIG. 2 while the intermediate tape section 33 and the third self-adhesive agent 49 respectively correspond to the intermediate tape section 33 and the third self-adhesive agent 49 in FIG. 2. Of two tape fasteners 30 obtained from a single unit 67 shown in FIG. 6, the one lying on the right side with respect to the imaginary line A is folded in a Z-shape and the one lying on the left side with respect to the imaginary line A is folded in an inverted Z-shape.

Assumed that the tape unit 67 is fed with elastic tension in its longitudinal direction in the step of FIG. 6, an amount of contraction of the top- and backsheets 2, 3 occurring in the vicinity of the lateral edges 13 of the diaper 1 may be adjusted to be larger than an amount of contraction occurring in the upper tape section 31 of the tape fastener 30, preferably by 0.7 mm or more after the continuum of diaper 65 has been cut together with the tape unit 67 to obtain the diaper 1 shown in FIG. 1.

In the process for continuously making the individual diapers 1, cutting of the web 63 being in a stretched state together with the tape unit 67 causes only the web 63 to contract or causes the web 63 to contract by an amount larger than an amount by the tape unit 67 contacts. With a consequence, the outer end portion 37 of the tape fastener 30 spontaneously extends outward beyond the lateral edge 13.

Figure 7A:
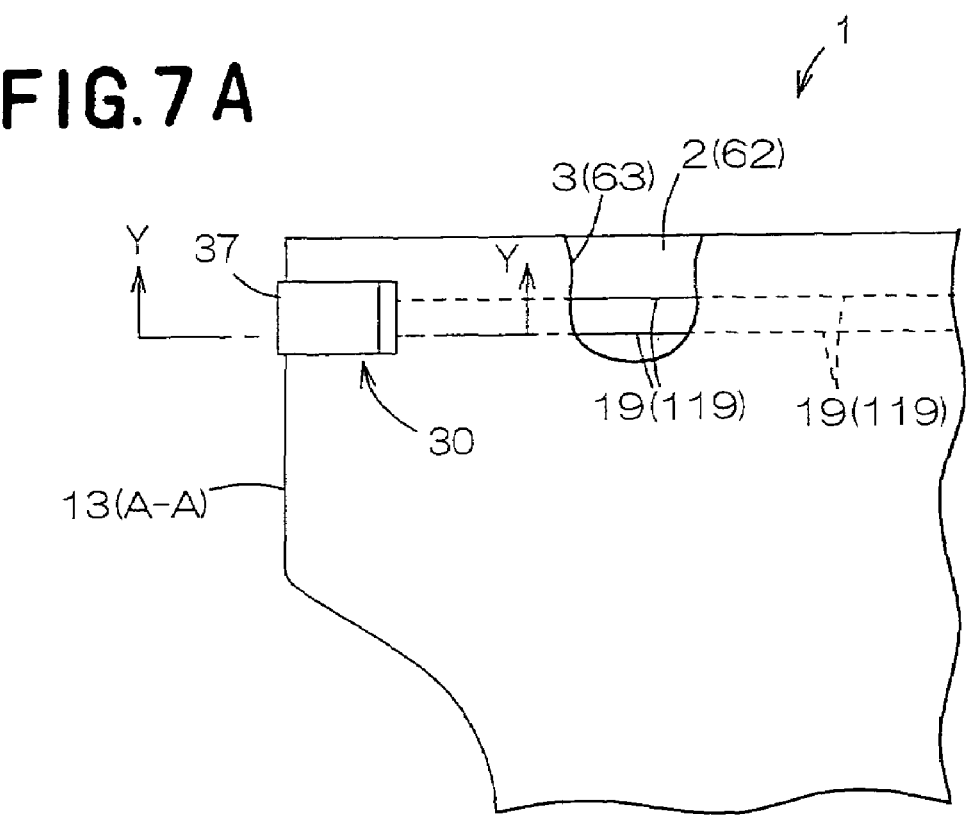
FIG. 7A is a diagram illustrating important parts of the diaper by the process partially different from the process of FIG. 5
Figure 7B:
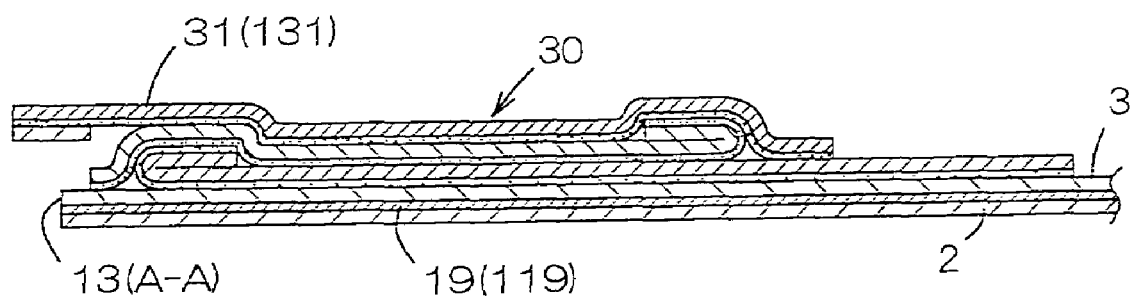
FIG. 7B is a sectional view taken along a line Y-Y in FIG. 7A.

Of FIG. 7A and FIG. 7B, FIG. 7A illustrates important parts of the diaper 1 obtained by shifting the units 67 and/or the elastic members 119 in the course of the process of FIG. 5 so that the tape fasteners 30 may overlie the waist-surrounding elastic members 19 with the backsheet 3 therebetween and FIG. 7B illustrates a section thereof as taken along a line Y-Y. In the steps (1) and (2) illustrated by FIG. 5, the elastic members 119 are in a stretched state between each pair of the adjacent imaginary lines A, A and bonded to the inner surface of the web 62 and/or the web 63. In the step (3), when the elastic members 119 contract in the vicinity of the line A-A as the continuum of diapers 65 is cut, the top- and backsheets 2, 3 also contract to form gathers. The tape fastener 30, on the other hand, does not contract and, as will be seen in FIG. 7B, the tape fastener 30 extends outwardly beyond the lateral edge 13 by an amount of contraction occurring in the top- and backsheets 2, 3. The tape fasteners 30 for the diaper 1 obtained in this manner have the same function as those for the diaper 1 obtained in the manner illustrated by FIG. 5. In this diaper 1, the elastic members 19 contract in the direction opposed to the direction in which the tape fasteners 30 are unfolded so that a high peeling force is exerted between each pair of the adjacent tape sections and facilitates these tape sections to be peeled off one from another as the tape fasteners are unfolded. It is also possible to handle the elastically stretchable web in a stretched state as the web 62 in FIG. 5 to obtain the topsheet 2 in FIGS. 7A and 7B. In this case, the web 62 elastically contracts together with the elastic members 119 as the web 62 is cut along the imaginary lines A, A.

FIG. 8 is a view similar to FIG. 2 but showing one preferred embodiment of this invention. In the tape fastener 30 of this diaper 1, the inner end portion 36 of the upper tape section 31 terminates on the inner end portion 46 of the intermediate tape section 33 without extending inwardly beyond the inner end portion 46 of the intermediate tape section 33 to the inside of the diaper 1.

FIGS. 9 and 10 are views similar to FIG. 2 but showing the other two preferred embodiments of this invention. The tape fastener 30 shown in FIGS. 9 and 10 comprises the upper tape section 31 and the lower tape section 932. Referring to FIG. 9, the inner end portion 941 of the lower tape section 932 is folded upwardly and firmly bonded to the lower surface of the upper tape section 31 by means of the first adhesive agent 44 while the outer end portion 942 of the lower tape section 932 is folded downwardly and firmly bonded to the upper surface of the backsheet 3 by means of the first adhesive agent 44. The upper tape section 31 is similar to the upper tape section 31 shown in FIG. 2 in that the inner end portion 36 thereof extends inwardly beyond the inner end portion 941 of the lower tape section 932 to the inside of the diaper 1 and temporarily bonded to the backsheet 3 by means of the second self-adhesive agent 39. The outer end portion 37 at least partially extends outwardly beyond the lateral edge 13 of the diaper 1. With this tape fastener 30, the outer end portion 37 may be taken between the fingers and pulled outwardly away from the diaper 1 in the direction indicated by the arrow P to peel off the inner end portion 36 of the upper tape section 31 from the backsheet 3 and thereby to extend the upper and lower tape section 31, 932 outwardly from the backsheet 3. In the tape fastener 30 shown in FIG. 10, the lower tape section 932 rectilinearly extends with both its inner end portion 941 and its outer end portion 942 not folded and these end portions 941, 942 are firmly bonded to the upper tape section 31 and the backsheet 3 by means of the first adhesive agent 44. This tape fastener 30 also may be pulled in the direction P to peel off the inner end portion 36 of the upper tape section 31 from the backsheet 3 and to extend the upper tape section 31 and the lower tape section 932 outwardly beyond the lateral edge 13 of the diaper 1. As will be understood from FIGS. 9 and 10, this tape fastener 30 comprises the upper tape section 31 having the deformable outer end portion 37 to be taken between the fingers and the lower tape section 932 having the inner end portion 942 for fixation to the backsheet 3 so that these end portions 37, 942 may define longitudinally opposite end portions as the upper and lower tape sections 31, 932 are unfolded from each other. This embodiment allows the intermediate tape section 33 in FIG. 2 to be eliminated. However, this tape fastener 30 is shorter than that according to the previously described embodiment by the length of the intermediate tape section 33. While the tape fastener 30 shown in FIGS. 9 and 10 has its construction simpler than those shown in FIGS. 2 and 8 and is available at a correspondingly lower cost, the backsheet 3 is apt to be damaged as the outer end portion 37 of the tape fastener 30 is pulled to peel off the upper tape section 31 from the backsheet 3.

Figure 11:
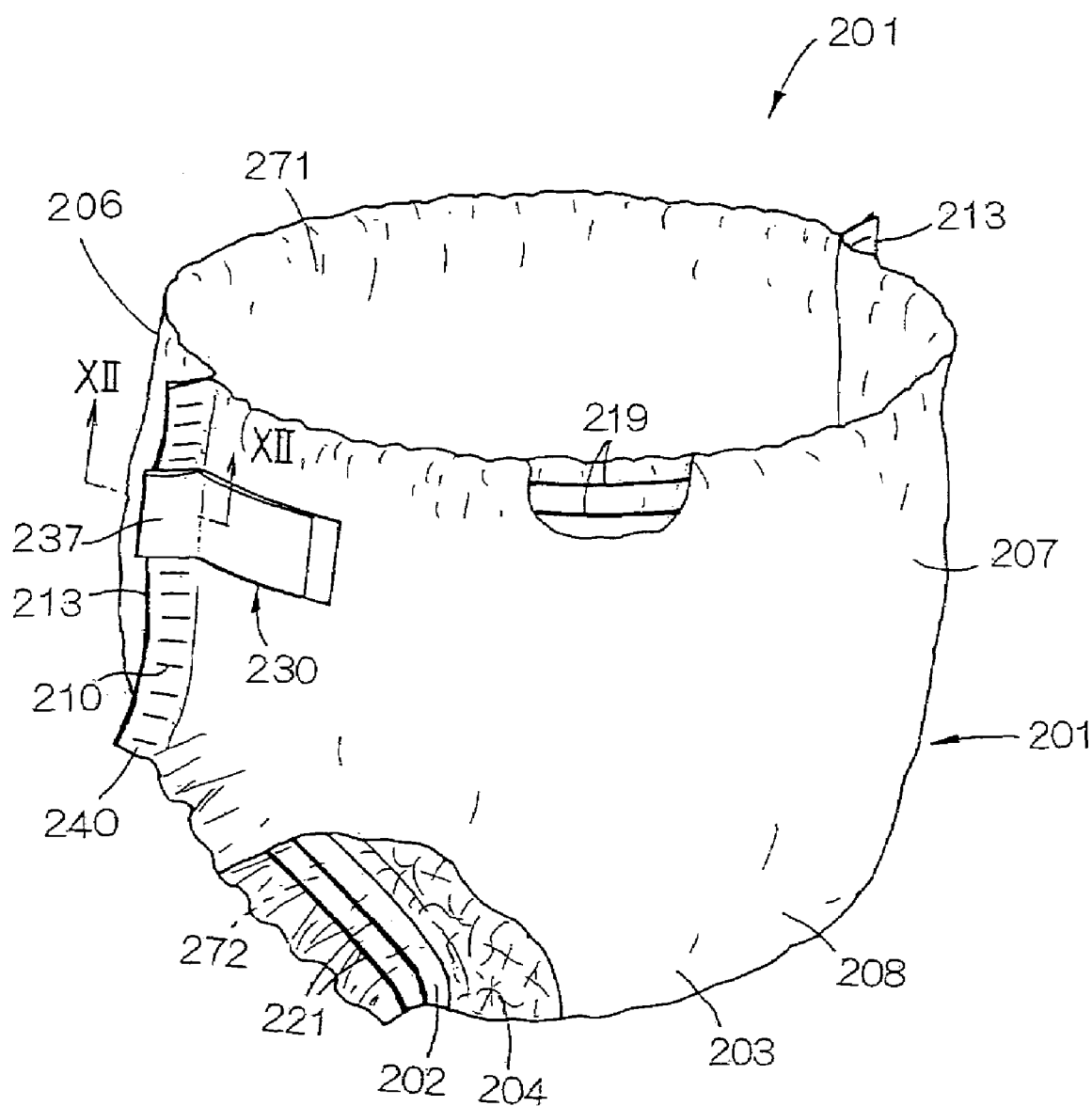
FIG. 11 is a partially cutaway perspective view showing a pants-type disposable diaper as another typical embodiment of this invention.

FIG. 11 is a partially cutaway perspective view showing a pants-type disposable diaper 201 as another typical embodiment of this invention. The diaper 201 comprises the liquid-pervious topsheet 202, the liquid-impervious backsheet 203 and the liquid-absorbent core 204 interposed between these two sheets 202, 203 so as to form the front waist region 206, the rear waist region 207 and the crotch region 208. The front and rear waist regions 206, 207 have transversely opposite lateral edges 213 overlaid and joined together at the zones 210 arranged intermittently along these lateral edges 213 in the vertical direction so as to define the waist-hole 271 and the leg-holes 272. These holes 271, 272 are provided along peripheral edges thereof with the waist-surrounding elastic members 219 and the leg-surrounding members 221, respectively, attached in a stretched state thereto. In the vicinity of the lateral edges 213 of the rear waist region 207, the tape fasteners 230 like the tape fastener 30 shown in FIG. 2 are attached to the diaper 201. The outer end portions 237 of the respective fasteners 230 partially extend outwardly beyond the respective lateral edges 213 of the diaper 201.

Figure 12:
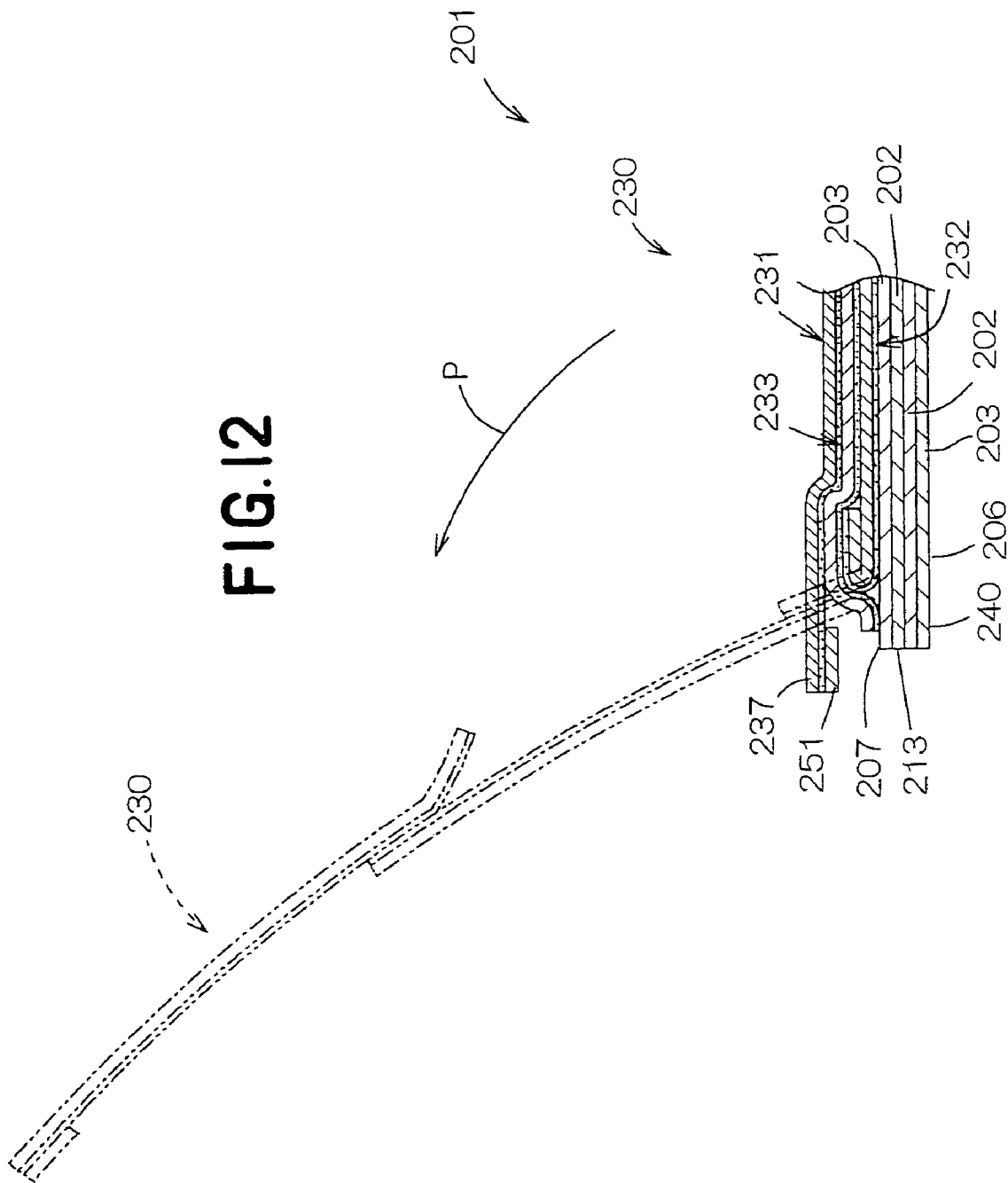
FIG. 12 is a sectional view taken along a line XII-XII in FIG. 11.

FIG. 12 is a sectional view taken along a line XII-XII in FIG. 11. The front and rear waist regions 206, 207 of the diaper 201 are overlaid together in the vicinity of the lateral edges 213 of these regions 206, 207. The top- and backsheets 202, 203 of the front and rear waist regions 206, 207 are joined together at the zones 210 to form flat laminated portions 240 extending laterally of the diaper 201 (See FIG. 11 also). Portions of the tape fastener 230 similar to those of the tape fastener 30 shown in FIG. 2 are designated by the similar reference numerals added with 200. In this diaper 201, the outer end portion 237 of the upper tape section 231 constituting the tape fastener 230 extend outwardly in the transverse direction of the diaper 201 beyond the lateral edge 213 defined by the laminated portion 240 of the front and rear waist regions 206, 207. This feature facilitates the outer end portion 237 of the tape fastener 240 to be taken between the fingers and thereby enables the outer end portion 237 taken between the fingers to be pulled as indicated by imaginary lines in the direction P to the front waist region 206 (See FIG. 13).

Figure 13:
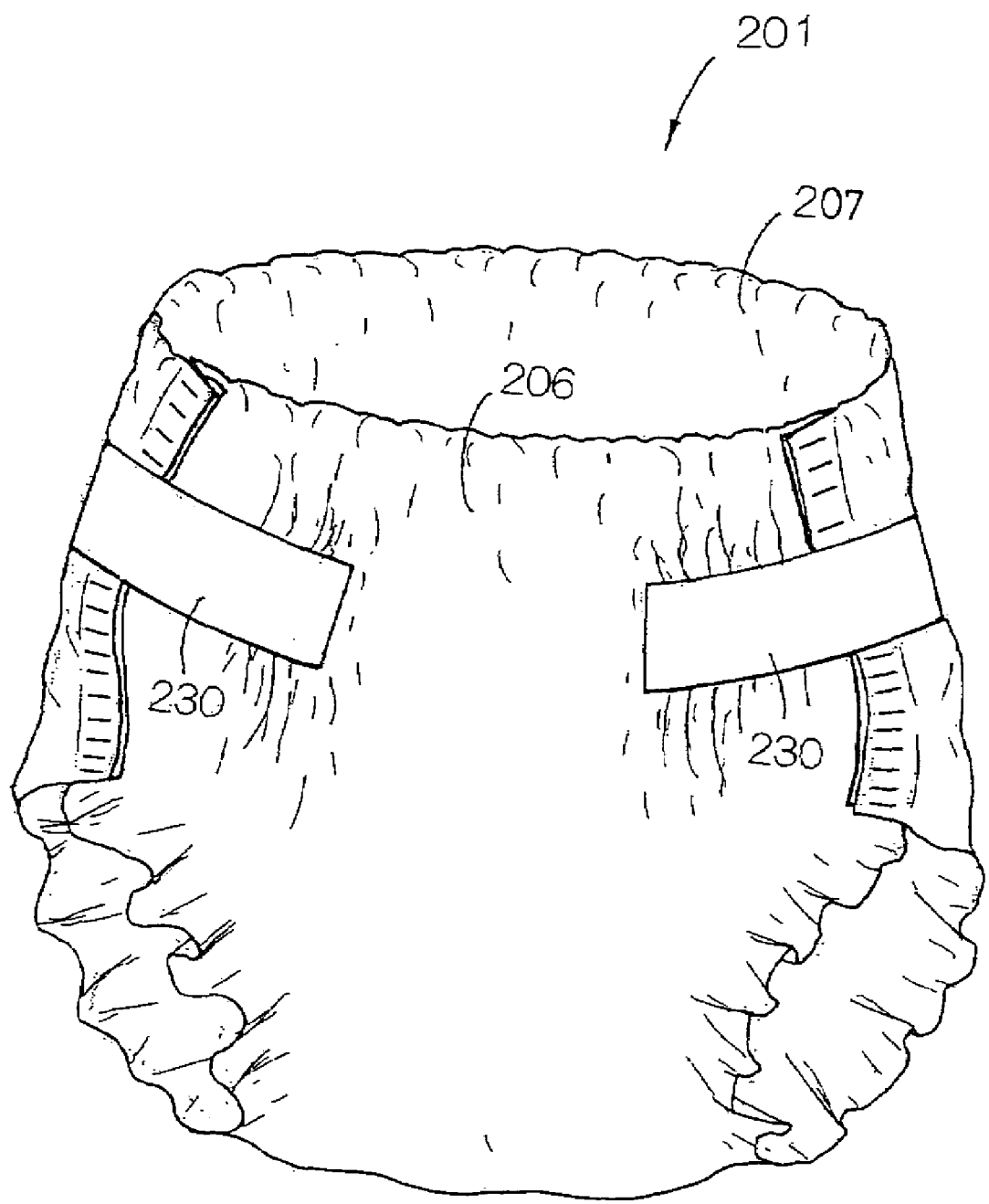
FIG. 13 is a perspective view of the pants-type disposable diaper to illustrate a manner in which the tape fasteners are used.

FIG. 13 is a perspective view of the pants-type disposable diaper to illustrate a manner in which the tape fasteners 230 in the diaper 201 are used. In the diaper 201 shown in FIG. 13, overabundance possibly present in the waist-surrounding direction by tucking such overabundance utilizing the tape fasteners 230 extending from the rear waist region 207 so that the front waist region 206 may be pulled toward the rear waist region 207. Like the tape fasteners 30 shown in FIG. 4, these tape fasteners 230 also can be used to roll up the used diaper for disposal.

While this invention has been described on the basis of the disposable diaper in reference to the accompanying drawings, it should be understood that this invention is applicable also to the other disposable wearing articles such as diaper for incontinence patient and training pants.

The disposable wearing article according to this invention has advantageous effects that the outer end portions of the respective tape fasteners adapted to be taken between the fingers extend outwardly beyond the lateral edges of the article. This feature facilitates the tape fasteners to be taken between the fingers. The process according to this invention for making such a disposable wearing article includes the step of elastically contracting the backsheet to which the tape fasteners are attached and thereby enables the outer end portions of the respective tape fasteners for taking them between the fingers to extend outwardly beyond the lateral edges of the wearing article.

What is claimed is:

1. A disposable wearing article, comprising:
   a wearer-facing surface adapted to face a wearer's body and a garment-facing surface adapted to face away from the wearer's body;
   front and rear edges extending in a transverse direction of said article, and a pair of lateral edges extending in a longitudinal direction orthogonal to said transverse direction;
   a crotch region, a front waist region extending forwardly in the longitudinal direction from said crotch region to said front edge, and a rear waist region extending rearwardly in the longitudinal direction from said crotch region to said rear edge; and a pair of folded tape fasteners respectively attached to the lateral edges of said front or rear waist region;

wherein each of said folded tape fasteners has a fixed end portion permanently joined to said garment facing surface, and a free end portion adapted to be gripped by fingers so that said folded tape fastener can be unfolded, by pulling said gripped free end portion, to a unfolded state, said free end portion having at least a part extending in the transverse direction outwardly beyond the respective lateral edge, and upper and lower surfaces of said part being free of adhesive material;

wherein each of said folded tape fasteners further comprises:

a first tape section defining a top layer of said folded tape fastener, said first tape section having said free end portion and a first end portion which is opposed to and located inward from said free end portion in the transverse direction, and a second tape section underlying said first tape section so as to face said garment facing surface, said second tape section having said fixed end portion and a second end portion which is opposed to and located outward from said fixed end portion in the transverse direction and is connected to said first end portion of said first tape section, wherein said first end portion of said first tape section is directly releasably bonded to said fixed end portion of said second tape section; and wherein said garment facing surface to which said tape fasteners are attached is made of a sheet being elastically stretchable in said transverse direction.

2. The disposable wearing article according to claim 1, wherein each of said folded tape fasteners further comprises a third tape section interposed between said first tape section and said second tape section to connect said first and second tape sections to each other, said third tape section having a third end portion connected to said first end portion of said first tape section, a fourth end portion which is opposed to and located outward from said third end portion in the transverse direction and is connected to said second end portion of said second tape section, and an intermediate portion defined between said third and fourth end portions and releasably joined by an adhesive layer, which is positioned between said first and third tape sections, to said first tape section so that said first, second and third tape sections define a Z- or inverted Z-shape of said folded tape fastener.

3. The disposable wearing article according to claim 2, wherein both said first end portion of said first tape section and said fixed end portion of said second tape section extend inwardly beyond said third end portion of said third tape section in said transverse direction and are directly releasably joined to each other.

4. The disposable wearing article according to claim 2, wherein said fourth end portion of said third tape section extends outwardly beyond said second end portion of said second tape section in said transverse direction and is directly joined to the garment facing surface.

5. The disposable wearing article according to claim 1, wherein said disposable wearing article is a pants-type disposable diaper, said front and rear waist regions being connected to each other in vicinities of said lateral edges so as to define a waist-hole and a pair of leg-holes.

6. The disposable wearing article according to claim 1, further comprising, in said front and rear waist regions and said crotch region, a liquid-absorbent core and flaps formed from sheet members extending outwardly in the transverse direction from a peripheral edge of said core, wherein said tape fasteners are attached to said garment facing surface in said flaps.

7. The disposable wearing article according to claim 1, further comprising:

elongated elastic members which are attached in a stretched state to the one of said front and rear waist regions provided with said tape fasteners so as to extend in said transverse direction between said lateral edges of said waist region;

said tape fasteners are attached to said garment facing surface in said front or rear waist region so as to overlap end portions of said elastic members; and the folded tape member of each of said tape fasteners is unfoldable to a unfolded state, in which the unfolded tape member extends longitudinally in the transverse direction, by pulling said free end portion outwardly in the transverse direction, thereby simultaneously stretching the elastic members in the transverse direction prior to putting the article on a wearer.

8. The disposable wearing article according to claim 1, wherein said free end portions at least partially extend outwardly beyond the respective lateral edges by 0.7 mm or more.

* * * * *